United States Patent [19]
Koch et al.

[11] Patent Number: 5,443,059
[45] Date of Patent: Aug. 22, 1995

[54] ULTRASONIC ATOMIZER WITH A METERING UNIT

[75] Inventors: Jochim Koch, Ratzeburg, Germany; Bambang Oetomo, Groningen, Netherlands

[73] Assignee: Dragerwerk AG, Lubeck, Germany

[21] Appl. No.: 183,046

[22] Filed: Jan. 14, 1994

[30] Foreign Application Priority Data

Jan. 15, 1993 [DE] Germany .............. 43 00 880.1

[51] Int. Cl.⁶ .............................................. A61M 11/00
[52] U.S. Cl. ...................... 128/200.16; 128/203.12; 128/204.18; 128/204.23
[58] Field of Search ............ 128/200.16, 204.18, 128/203.12, 200.14, 203.25, 200.22, 200.23, 204.23

[56] References Cited

U.S. PATENT DOCUMENTS

| | | | |
|---|---|---|---|
| 3,172,406 | 3/1965 | Bird et al. | 128/200.18 |
| 3,291,122 | 12/1966 | Engstrom | 128/200.16 |
| 3,360,664 | 12/1967 | Straube | 128/200.16 |
| 3,392,916 | 7/1968 | Engström et al. | 128/203.12 |
| 3,630,196 | 12/1971 | Bird et al. | 128/200.18 |
| 3,690,317 | 9/1972 | Millman | 128/200.16 |
| 3,812,854 | 5/1974 | Michaels et al. | 128/200.16 |
| 4,106,503 | 8/1978 | Rosenthal et al. | 128/203.12 |
| 4,109,863 | 8/1978 | Olson et al. | 128/200.16 |
| 4,186,737 | 2/1980 | Valenta et al. | 128/203.2 |
| 4,819,629 | 4/1989 | Jonson | 128/204.23 |
| 4,938,210 | 7/1990 | Shene | 128/200.23 |
| 5,063,922 | 11/1991 | Hakkinen | 128/200.16 |
| 5,156,776 | 10/1992 | Loedding et al. | 128/203.12 |
| 5,207,220 | 5/1993 | Long | 128/203.12 |
| 5,299,566 | 4/1994 | Davis et al. | 128/200.24 |
| 5,303,699 | 4/1994 | Bonassa et al. | 128/204.23 |
| 5,309,903 | 5/1994 | Long | 128/203.12 |
| 5,318,015 | 6/1994 | Mansson et al. | 128/200.22 |
| 5,322,057 | 6/1994 | Raabe et al. | 128/200.16 |

FOREIGN PATENT DOCUMENTS

3308819A1 9/1984 Germany.
3636669A1 5/1988 Germany.

*Primary Examiner*—Edgar S. Burr
*Assistant Examiner*—William J. Deane, Jr.
*Attorney, Agent, or Firm*—McGlew and Tuttle

[57] ABSTRACT

A device for generating an aerosol in the course of a respiration gas line, which leads from a respirator to a patient for the patient's artificial respiration. The dead space volume existing during the artificial respiration is minimized, and it is possible to arrange the generating device as close to the patient as possible in the course of the respiration gas line. In the interior space of the respiration gas line, an ultrasound generator unit (11, 12), which has a vibrating surface (14), above which a metering line (16) opens, and predeterminable amounts of the liquid to be atomized are delivered from a metering unit (16) outside the respiration gas line (6).

9 Claims, 1 Drawing Sheet

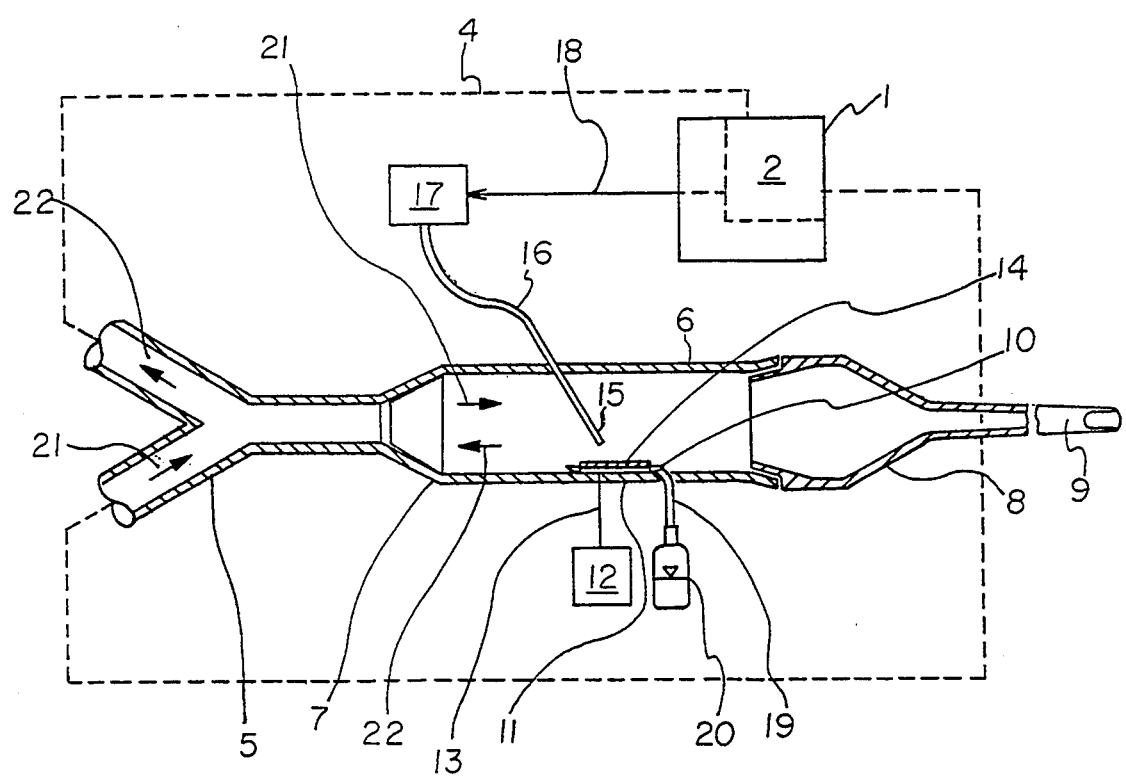

ULTRASONIC ATOMIZER WITH A METERING UNIT

FIELD OF THE INVENTION

The present invention pertains to a device for generating an aerosol, which is fed in the liquid form into an atomizing device, and the aerosol is sent via a respiration gas line to a connection part of a respirator, which performs inspiration and expiration strokes by means of a respiration gas delivery unit to ensure the artificial respiration of a patient.

BACKGROUND OF THE INVENTION

The humidification of a respiration gas, which is fed to a patient connected to a Y-piece and a tube through a respirator via a respiration gas line, is always necessary in order to prevent the lobes of the lung and the alveoli from drying out during long-term artificial respiration. Moreover, it is possible to introduce drugs in the form of aerosols into the lungs via the prior-art humidifying devices in order to treat lung diseases or to prevent pulmonary malfunctions. One particular aspect, namely, avoiding dead space volumes in the course of the respiration gas line by adding an atomizer, deserves careful attention, especially in connection with the artificial respiration of premature and newborn babies.

In a device for supplying aerosol into a patient's airways or lungs, which has become known from German Offenlegungsschrift No. DE-OS 36 36 669, an atomizing device, which entrains droplets from a liquid reservoir via a nozzle connected to a gas source and transports them into the respiration gas line, is provided in the inspiration line between a respirator and the patient. The additional gas source, which is formed by the nozzle operated with compressed air, changes the respiration gas volume delivered by the respirator, and it consequently must be taken into account in connection with the setting of the parameters of artificial respiration. In addition, the flow path for the aerosol generated by the nozzle, as well as the liquid reserve container make the dead space volume so large that this prior-art atomizing device is not suitable for the artificial respiration of premature and newborn babies. The expensive design, which has a large space requirement, makes it impossible to arrange the prior-art atomizer close to the patient.

Another prior-art atomizer according to German Offenlegungsschrift DE-OS 33 08 819 provides a heatable pressure vessel, into the interior space of which a liquid is fed and is evaporated there. The vapor thus generated is fed to the respiration gas line via a humidifying line and a controllable valve. This prior-art atomizer cannot be used close to the patient because of its bulky design and its weight, either.

SUMMARY AND OBJECTS OF THE INVENTION

The primary object of the present invention is to improve an atomizer of the above-described type such that the dead space volume existing during the artificial respiration is minimized and its compact design makes it possible to arrange it as close to the patient as possible in the course of the respiration gas line.

This object is attained by providing an ultrasonic atomizer in the interior space of the respiration gas line, wherein this ultrasonic atomizer has a vibrating surface, which is induced to perform ultrasonic vibrations, and a metering line, which is connected to a metering unit arranged outside the respiration gas line and meters the liquid to be atomized onto the vibrating surface, is arranged at the level of and at a spaced location from the vibrating surface.

The advantages of the present invention are essentially the fact that an ultrasound generator, the vibrating surface (by which predetermined amounts of the liquid to be atomized are metered), need be installed only in the already existing line section of the respiration gas line. No appreciable volume, which would increase the dead space, need be connected to the respiration gas line for this. The small amounts of liquid to be atomized are generated directly in the respiration gas line, so that additional gas supply, which is needed in the prior-art atomizers for generating the aerosol, is not necessary. Thus, the parameters of artificial respiration, which are set on the respirator, are influenced by the additional atomization only insignificantly. Since only small amounts of liquid must be atomized, the necessary components, namely, the ultrasound generator and the metering line, are of such a low weight that they can be installed directly in the vicinity of the patient to be subjected to artificial respiration, preferably on a Y-piece.

Any prior-art device for metering liquids, e.g., a self-priming reciprocating pump drawing the liquid to be atomized from a reservoir, or even a spray pump, whose feed mechanism is actuated by a controlled drive, may be used as the metering unit.

Since atomization or aerosol formation is necessary only during the inspiration stroke, the metering unit and the ultrasound generator can advantageously be connected to a control unit, which either forms an integral component of the respirator, or forms a separate unit, which also actuates the metering unit and/or the ultrasound generator during the performance of the inspiration stroke. The metering stroke can be triggered and the ultrasound generator can be induced in phase with the triggering of the inspiration stroke, or with a time shift or phase shift. The desired phase shift can be set on the control unit. Since the metering and the aerosol generation or the atomization or spraying take place directly at the connection piece leading to the patient, the aerosol does not need to travel over long distances in the respiration gas line before it finally reaches the patient, so that no appreciable condensation or deposition takes place, as a result of which the liquid to be atomized can be metered economically. This property is effective especially when a surfactant is used as the liquid to be atomized. Such liquids are needed as surface-active substances on the surface of the alveoli in order to prevent the lung surface from collapsing during expiration in certain pathological conditions of pulmonary airways. The extremely high price of such liquids, as well as that of other drugs to be atomized, requires an economic, and yet effective administration for a corresponding therapy, which is made possible by the present invention.

Nevertheless, it can happen that non-atomized liquid is left behind, which is preferably collected by a tray accommodating the piezoceramic portion of the ultrasound generating unit.

To remove the non-atomized liquid from the respiration gas line, it is useful to provide the tray with a liquid drain. Since overpressure is normally always present in the respiration gas line, the liquid is automatically pressed by this pressure out of the drain and into a collection vessel, which is equipped with a pressure relief valve.

To simplify the use and to facilitate the replacement of the atomizing unit, formed by an ultrasound generator and a metering line, the respiration gas line containing the piezoceramic portion of the ultrasound generating unit may be designed as a replaceable plug-in module. This is connected to the Y-piece and can easily be replaced if necessary. When the plug-in module is replaced, it is not necessary to replace the reservoir for the liquid at the same time, because the metering unit, arranged outside the respiration gas line, can always be connected or removed separately by simply separating the metering line from the plug-in module. This also entails special advantages in terms of treatment for the personnel or the user, because the independent metering unit can be transferred from one place of treatment when atomization is no longer necessary or must be discontinued. Thus, it is not necessary from the outset to equip each respiration gas line of each patient with an atomizing device and to supply it with an expensive atomization liquid, but the same reservoir or metering unit can be transferred from one place of treatment to the next.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only figure is a cross sectional partially schematic view of the ultrasonic atomizer and metering unit according to the invention.

DETAILED DESCRIPTION OF THE PREFERRED EMBODIMENT

The only figure shows a respirator 1 with a control unit 2 for performing inspiration strokes and expiration strokes in an inspiration line 3 and in an expiration line 4, respectively. The two lines 3, 4 unite in a Y-piece 5 to form a respiration gas line 6, designed as a plug-in module, which is connected at one of its ends to the Y-piece 5 with a snap-in connection 7, and is continued on its other side via a tube connector 8 with a tube 9. The tube 9 is used for introduction into the trachea of a patient (not shown). The respiration gas line 6 carries a tray 10, in which a piezoceramic 11 is accommodated. The piezoceramic 11 is connected to an ultrasound signal generator 12 via an exciting line 13. The piezoceramic 11 and the ultrasound signal generator 12 together form the ultrasound generating unit. The piezoceramic 11 is provided with a vibrating surface 14 on its side facing the interior space of the respiration gas line 6. The opening 15 of a metering line 16 ends above and at a spaced location from the vibrating surface 14. The metering line 16 passes through the wall of the respiration gas line 6 and originates from a metering unit 17. The metering unit 17 meters the liquid to be atomized on the vibrating surface 14 in predeterminable amounts from a reservoir (not shown). To initiate a metering stroke by the metering unit 17, the metering unit 17 is connected to the control unit 2 via a control line 18. The control unit 2 is represented symbolically by a broken line within the respirator 1, and it forms only part of the entire respirator 1. The tray 10 is provided with a liquid drain 19, which ends in a collection vessel 20.

In the ready-to-operate state, the metering line 16 is filled with the liquid to be metered, and the metering unit 17 waits for a control command from the control line 18 to perform a metering stroke. This is initiated either continuously, in phase with, or with a phase shift in relation to the inspiration stroke, which is triggered by the metering unit 2 in the respirator 1. Respiration gas flows during the inspiration stroke through the inspiration line 3 according to the direction arrows 21 in the direction of inspiration, i.e., in the direction of the tube 23. The metering unit 17 now delivers a small amount of liquid from the integrated reservoir (not shown) into the metering line 16, which is then distributed onto the vibrating surface 14, which is induced to perform vibrations, and it is atomized into very fine aerosol droplets there during the inspiration as a consequence of the ultrasonic vibrations. The respiration gas is delivered by the respiration gas flow into the tube 9 together with the atomized liquid. After the end of the inspiration stroke, the control unit 2 triggers the expiration stroke, during which the respiration gas is blown off in the direction of the expiration arrow 22 into the expiration line 4. The control unit 2 can be adjusted such that atomization is performed by the cooperation of the metering unit 17 and the ultrasound generator unit 11, 12 either with each inspiration stroke or only after every second, third inspiration stroke, etc.

While a specific embodiment of the invention has been shown and described in detail to illustrate the application of the principles of the invention, it will be understood that the invention may be embodied otherwise without departing from such principles.

What is claimed is:

1. A device for generating an aerosol, comprising:

a tube for connection to a patient;

a Y-piece;

a respiration gas line extending between said tube and said Y-piece and accommodating two way flow of respiration gas;

a respirator including respiration gas delivery means for performing inspiration and expiration strokes for artificial respiration of a patient, said respirator including a connection part including an inspiration gas line, an air expiration gas line and said Y-piece, said inspiration line being connected to one branch of said Y-piece, said expiration line being connected to another branch of said Y-piece and said respiration gas line being connected to a central part of said Y-piece;

an ultrasound generator unit including a vibrating surface, said vibrating surface being provided in an interior space of said respiration gas line in an immediate vicinity of said Y-piece, said vibrating surface being induced to perform ultrasonic vibrations;

a metering line extending into said respiration gas line at an opening in said respiration gas line, said opening being at a level of and at a spaced location from said vibrating surface; and a metering unit connected to said metering line for metering a liquid to be atomized onto said vibrating surface, said metering unit being arranged outside of said respiration gas line.

2. A device according to claim 1, further comprising:

respirator control unit means for controlling the artificial respiration of the patient, said control unit means being connected to said metering unit for causing said ultrasound generator unit to perform atomization when an inspiration stroke is performed, said atomization being triggered in a predetermined phase relation to the triggering of said inspiration stroke.

3. A device according to claim 1, wherein: said respiration gas line containing said ultrasound generator unit comprises a replaceable plug-in module connected to said Y-piece.

4. A device according to claim 1, wherein: said liquid to be atomized is a surfactant.

5. A device according to claim 1, further comprising: a tray for collecting non-atomized liquid, said vibrating surface being accommodated in said tray.

6. A device according to claim 5, wherein:
said tray is provided with a liquid drain.

7. A device according to claim 1, wherein said ultrasound generator unit further comprises an ultrasound signal generator, generating a signal for inducing said vibrating surface to perform ultrasonic vibrations.

8. A device, comprising:
a tube for connection to a patient; a Y-piece;
a respiration gas tube;
a respirator including respiration gas delivery means for performing inspiration and expiration stokes and a connection part including an inspiration gas line, an air expiration gas line and said Y-piece, the inspiration line being connected to one branch of said Y-piece, said expiration line being connected to another branch of said Y-piece and said respiration gas tube being connected to a central part of the Y-piece;

said respiration gas tube being in the form of a plug in unit connected to said connection part, said plug in unit and said connection part together defining a respiration gas line;

an ultrasound generator unit including a vibrating surface, said vibrating surface being provided in said plug-in unit of said respiration line, said vibrating surface being induced to perform ultrasonic vibrations, said plug in unit being connected directly to said Y-piece to position said vibrating surface immediately adjacent to said Y-piece;

a metering line extending into said plug-in unit at an opening defined in said plug-in unit, said opening being at a level and at a spaced location from said vibrating surface; and a metering unit connected to said metering line for metering a liquid to be atomized onto said vibrating surface, said metering unit being arranged outside of said respiration gas line.

9. A device according to claim 8, further comprising: respirator control unit means for controlling the artificial respiration of the patient, said control unit means being connected to said metering unit for causing said ultrasound generator unit to perform atomization when an inspiration stroke is performed, said atomization being triggered in a predetermined phase relation to the triggering of said inspiration stroke.

* * * * *